US009503809B2

(12) United States Patent
Mikami et al.

(10) Patent No.: US 9,503,809 B2
(45) Date of Patent: Nov. 22, 2016

(54) BEAM-FORMING DEVICE

(75) Inventors: Takashi Mikami, Tokyo (JP); Tomoharu Awano, Tokyo (JP)

(73) Assignee: Mitsubishi Electric Corporation, Tokyo (JP)

( * ) Notice: Subject to any disclaimer, the term of this patent is extended or adjusted under 35 U.S.C. 154(b) by 0 days.

(21) Appl. No.: 14/411,980

(22) PCT Filed: Aug. 6, 2012

(86) PCT No.: PCT/JP2012/069997
§ 371 (c)(1),
(2), (4) Date: Dec. 30, 2014

(87) PCT Pub. No.: WO2014/024248
PCT Pub. Date: Feb. 13, 2014

(65) Prior Publication Data

US 2015/0181329 A1 Jun. 25, 2015

(51) Int. Cl.

| | |
|---|---|
| ***A61F 11/06*** | (2006.01) |
| ***H04R 1/40*** | (2006.01) |
| ***H04R 3/00*** | (2006.01) |

(52) U.S. Cl.
CPC *H04R 1/40* (2013.01); *H04R 3/00* (2013.01); *H04R 3/005* (2013.01); *H04R 2201/403* (2013.01); *H04R 2499/13* (2013.01)

(58) Field of Classification Search
CPC .................. H04R 3/005; H04R 25/407; H04R 1/406; H04R 1/1083; H04R 2430/23;
(Continued)

(56) References Cited

U.S. PATENT DOCUMENTS

2007/0076898 A1* 4/2007 Sarroukh ............. G10K 11/341 381/92
2011/0313763 A1* 12/2011 Amada .................. H04R 3/005 704/233
(Continued)

FOREIGN PATENT DOCUMENTS

JP 8 122424 5/1996
JP 10 171487 6/1998
(Continued)

OTHER PUBLICATIONS

Ohga, J. et al., "Acoustic systems and digital technology", The Institute of Electronics, Information and Communication Engineers, pp. 181-186, (Mar. 25, 1995).
(Continued)

*Primary Examiner* — Akelaw Teshale
(74) *Attorney, Agent, or Firm* — Oblon, McClelland, Maier & Neustadt, L.L.P.

(57) ABSTRACT

A beam-forming device includes a first target sound blocker 103 and a second target sound blocker 104 that remove a target signal having a correlation mutually from a first sound signal $x_1$ and a second sound signal $x_2$ which are converted by first and second microphones 101 and 102, a phase synchronizer 105 that synchronizes the phases of the first sound signal $x_1$ and the second sound signal $x_2$ and synthesizes these sound signals by using information acquired when the first target sound blocker 103 removes the target signal, and a noise learner 106 that learns a noise component included in an output signal of the phase synchronizer 105 from signals from which the target signal is removed by the first target sound blocker 103 and the second target sound blocker 104.

8 Claims, 5 Drawing Sheets

(58) Field of Classification Search

CPC .................. H04R 2410/01; H04R 1/08; H04R 2201/403; H04R 2499/13; H04R 25/405; H04R 1/326; H04R 2203/12; H04R 17/02; H04R 2499/15; H04R 29/005; H04R 29/006

USPC ...... 379/92, 66, 315, 71.6, 313, 22, 26, 309, 379/318, 71.1, 74, 86, 94.2, 23.1, 300, 304, 379/312, 314, 316, 317, 320, 323, 334, 338, 379/375, 381, 71.11, 71.2, 71.7, 91

See application file for complete search history.

(56) References Cited

U.S. PATENT DOCUMENTS

2012/0243559 A1* 9/2012 Pan ....................... H04J 3/1605 370/503
2013/0114835 A1* 5/2013 Holmberg ............ H04R 25/407 381/313
2013/0271902 A1* 10/2013 Lai ........................... H04R 1/02 361/679.01
2015/0181329 A1* 6/2015 Mikami ................. H04R 3/005 381/71.11

FOREIGN PATENT DOCUMENTS

| | | |
|---|---|---|
| JP | 2006 217649 | 8/2006 |
| JP | 2010 152021 | 7/2010 |
| JP | 2010 160245 | 7/2010 |
| WO | 2010 109708 | 9/2010 |

OTHER PUBLICATIONS

International Search Report Issued Nov. 13, 2012 in PCT/JP12/069997 Filed Aug. 6, 2012.

* cited by examiner

BEAM-FORMING DEVICE

FIELD OF THE INVENTION

The present invention relates to a beam-forming device that carries out beamforming in order to acquire a signal in which a target signal is enhanced from a plurality of microphone signals.

BACKGROUND OF THE INVENTION

In order to construct a call system, such as a vehicle-mounted handsfree system, in a high-noise environment or an environment where a plurality of signal sources exist, a technique of separating and extracting only a signal of a specific signal source (speaker) is required. A beamformer is provided as one example of this technique. The beamformer enhances a signal in a target direction by adding signals of multiple channels provided by a microarray, and includes a fixed beamformer and an adaptive beamformer.

The simplest fixed beamformer is based on Delay and Sum, and is comprised of microphones 901 and 902 of two channels, a signal delaying unit 903, and a delay summing unit 904, as shown in FIG. 6. While this Delay and Sum generally requires only a small amount of computations, a problem with the Delay and Sum is that when it is difficult to use a large number of microphones, such as when the Delay and Sum is used for vehicle-mounted use, a sidelobe is large, the method is not effective in a reverberation environment, and adequate directivity is not acquired for a low frequency region.

In order to improve the directivity in a low frequency region, it is necessary to lengthen the array length of the entire microphone array. For example, when a main lobe is made to have directivity of about ±10 degrees for a 1000-Hz sound, it is necessary to make the array length be about 2 m. A further problem is that when the array length is increased by simply lengthening the intervals of the microphone array, a grating lobe occurs in a direction other than the target direction, and the directivity degrades (refer to nonpatent reference 1). Therefore, another problem is that in order to suppress the grating lobe and maintain the directivity in the low frequency region, it is necessary to arrange a large number of microphones densely, and hence the fixed beamformer costs highly.

In contrast with this, the adaptive beamformer is based on a method of forming directivity in such a way that a noise sound source is located in a blind spot while holding the sensitivity in a target direction at a constant level, and is effective also for a low frequency region and can carryout noise suppression in a reverberation environment. Although there are various methods for use in the adaptive beamformer, there is a generalized sidelobe canceller (GSC) as one of methods which can be assumed to be an extension of the Delay and Sum. The generalized sidelobe canceller is a beamformer that suppresses noise by using a fixed beamformer and an adaptive filter, and a typical Griffith-Jim type GSC using microphones of two channels is constructed as shown in FIG. 7. This GSC is comprised of microphones 901 and 902 of two channels, a signal delaying unit 903, a delay summing unit 904, a target sound blocker 905, and an adaptive filter 906, and the target sound blocker 905 carries out subtraction-type beamforming based on a subtraction of microphone signals. The adaptive filter 906 estimates a noise component by using an output of the target sound blocker 905, and determines a difference with an output of the delay summing unit 904.

It is considered that only a noise component in which a target signal is subtracted remains in the output of the subtraction-type beamformer, and the noise component can be removed from the result of the Delay and Sum by applying the output as an input to the adaptive filter. A problem is, however, that only the simple subtraction cannot sufficiently remove the target signal in many cases, and the adaptive filter cannot sufficiently remove the noise, but ends up removing the target signal.

As a measure against this problem, in a device disclosed by patent reference 1, a target sound blocker is constructed of an adaptive filter using an output of a fixed beamformer and microphone inputs, and is constructed in such a way as to remove a target signal from each of the microphone inputs. Because a signal from which the target sound is removed more sufficiently as compared with a simple subtraction-type beamformer is acquired, the noise suppression performance of the adaptive filter in the next stage can be improved.

RELATED ART DOCUMENT

Patent Reference

Patent reference 1: Japanese Unexamined Patent Application Publication No. H 08-122424

Nonpatent Reference

Nonpatent reference 1: “Acoustic systems and digital technology” written by Ohga Juro, Yamazaki Yoshio, Kaneda Yutaka, First Edition, The Institute of Electronics, Information and Communication Engineers, Mar. 25, 1995, pp. 181-186

SUMMARY OF THE INVENTION

Problems to be Solved by the Invention

A problem with the technique disclosed by above-mentioned patent reference 1 is that because the SN ratio (Signal to Noise Ratio) is improved by synchronizing the phases of a plurality of input signals by using a fixed FIR (Finite Impulse Response) filter or the like in a fixed beamformer, when the phase shift or the intensity differs or changes for each frequency band dependently upon a sound field environment, the phases cannot be synchronized with a high degree of accuracy and the performance of phase synchronization degrades.

The present invention is made in order to solve the above-mentioned problem, and it is therefore an object of the present invention to provide an improvement in the accuracy of phase synchronization of a plurality of input signals, and acquire an output signal having an improved SN ratio.

Means for Solving the Problem

In accordance with the present invention, there is provided a beam-forming device including: a first target sound blocker and a second target sound blocker that remove a target signal having a correlation mutually from a first sound signal and a second sound signal into which sounds collected by different microphones are converted respectively; a phase synchronizer that synchronizes the phases of the first sound signal and the second sound signal and synthesizes these sound signals by using information acquired when the first target sound blocker removes the target signal; and a noise learner that learns a noise component included in an output signal of the phase synchronizer from signals from which the target signal is removed by the first target sound blocker and the second target sound blocker.

Advantages of the Invention

According to the present invention, synchronization of the phases of the plurality of input signals can be carried out with a high degree of accuracy, and an output signal having an improved SN ratio can be acquired.

EMBODIMENTS OF THE INVENTION

Hereafter, in order to explain this invention in greater detail, the preferred embodiments of the present invention will be described with reference to the accompanying drawings.

Embodiment 1

Figure 1:
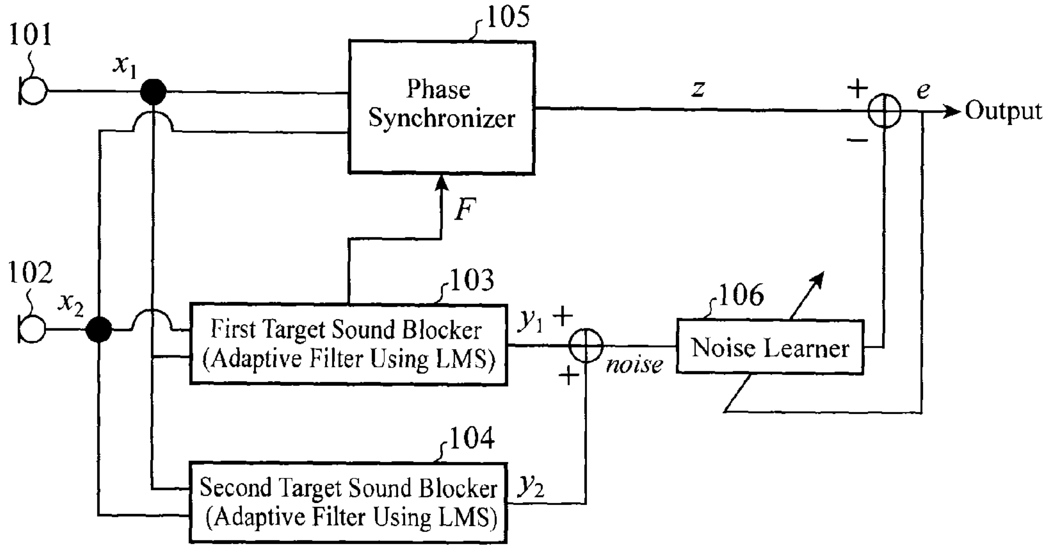
FIG. 1 is a view showing the structure of a beam-forming device in accordance with Embodiment 1.

FIG. 1 is a view showing the structure of a beam-forming device in accordance with Embodiment 1 of the present invention.

The beam-forming device in accordance with Embodiment 1 is comprised of a first microphone 101, a second microphone 102, a first target sound blocker 103, a second target sound blocker 104, a phase synchronizer 105, and a noise learner 106.

The first microphone 101 and the second microphone 102 convert an external sound into electric signals (a first sound signal and a second sound signal). The first target sound blocker 103 performs a process of blocking a target sound from a signal of the first microphone 101 by using a signal of the second microphone 102. The second target sound blocker 104 performs a process of blocking the target sound from the signal of the second microphone 102 by using the signal of the first microphone 101. The phase synchronizer 105 carries out phase synchronization between the input signals inputted thereto from the first microphone 101 and the second microphone 102 by using a processed result inputted thereto from the first target sound blocker 103. The noise learner 106 learns a noise component from an output signal of the phase synchronizer 105 by using a signal which is a mixture of signals outputted from the first target sound blocker 103 and the second target sound blocker 104.

Next, the operation of the beam-forming device in accordance with this Embodiment 1 will be explained.

Hereafter, an explanation will be made by taking, as an example, a case in which an adaptive filter using LMS (Least Mean Squares filter) is used for each of the first target sound blocker 103 and the second target sound blocker 104.

As shown in FIG. 1, the first target sound blocking section 103 receives, as its input, signals from the signal $x_1$ of the first microphone 101 to the signal $x_2$ of the second microphone 102, and determines a residual signal by using the LMS adaptive filter. As a result, a signal (target signal) included in both the first microphone 101 and the second microphone 102 and having a correlation can be removed from the signal $x_1$ of the first microphone 101.

When the signal of the first microphone 101 at a time n is expressed by $x_1(n)$ and the signal of the second microphone 102 at the time n is expressed by $x_2(n)$, the output of the first target sound blocker 103 is expressed by $y_1(n)$, and the filter coefficient of the LMS adaptive filter of the first target sound blocker 103 is expressed by $F(n)=[h_0(n), h_1(n), \ldots, h_{p-1}(n)]^T$, a signal $e_1(n)$ after sound removal is determined by using the following equations (1) to (3).

$$X_2(n)=[x_2(n),x_2(n-1), \ldots, x_2(n-p-1)]^T \quad (1)$$

$$e_1(n)=x_1(n)-y_1(n)=x_1(n)-F^T(n)\cdot X_2(n) \quad (2)$$

$$F(n+1)=F(n)+\mu\cdot e_1(n)\cdot X_2(n) \quad (3)$$

In the equation (3), μ is a constant for determining a learning speed and is a positive value smaller than 1. In the equation (1), p is the length of the LMS adaptive filter. In the equations (1) and (2), T shows a transposed matrix. As the length p of the LMS adaptive filter, a length of the order in which a sound signal has a correlation is used. Because the learning of the filter coefficient easily advances when the LMS adaptive filter has strong power, the learning advances during a sound interval, and a sound signal can be easily removed from the signal $x_1$ of the first microphone 101.

Similarly, the second target sound blocker 104 receives, as its input, signals from the signal $x_2$ of the second microphone 102 to the signal $x_1$ of the first microphone 101, and determines a residual signal by using the LMS adaptive filter. As a result, the signal (target signal) included in both the second microphone 102 and the first microphone 101 and having a correlation can be removed from the signal $x_2$ of the second microphone 102.

On the other hand, the phase synchronizer 105 synthesizes the signal $x_1$ of the first microphone 101 and the signal $x_2$ of the second microphone 102 by making them pass through an FIR filter. In this case, as the coefficient of the FIR filter, the filter coefficient F(n) of the LMS adaptive filter which the first target sound blocker 103 has learned is set up. Because the filter coefficient F(n) which has been learned by the first target sound blocker 103 is the one which is learned in such a way that the phase of the signal $x_2$ of the second microphone 102 is synchronized with that of the signal $x_1$ of the first microphone 101, a signal whose phase is synchronized with the signal $x_1$ of the first microphone 101 can be acquired by convolving the filter coefficient with the signal $x_2$ of the second microphone 102. More specifically, the signal $x_1$ of the first microphone 101 and the signal which is acquired by convolving the filter coefficient F(n) which the first target sound blocker 103 has learned with the signal $x_2$ of the second microphone 102 are added and averaged. The output signal z (n) of the phase synchronizer 105 at the time n is expressed by the following equation (4).

$$z(n)=(x_1(n)+F^T(n)\cdot X_2(n))/2 \quad (4)$$

Through the process by the phase synchronizer 105, beamforming of further enhancing the sound as compared with the Delay and Sum shown in the conventional example can be implemented.

Further, the output signal $y_1$ of the first target sound blocker 103 and the output signal $y_2$ of the second target sound blocker 104 are added to generate a noise signal noise, and this noise signal is inputted to the noise learner 106. The noise learner 106 receives this noise signal noise as its input, and learns a noise component included in the output signal z of the phase synchronizer 105 by using an NLMS (Normalized Least Mean Squares filter) adaptive filter that assumes the output signal z of the phase synchronizer 105 as the target signal. By subtracting the output signal of the noise learner 106 from the output signal z of the phase synchronizer 105, a signal e from which the noise is removed can be acquired.

When a sum signal which is the sum of the output signal $y_1$ of the first target sound blocker 103(*n*) at the time n and the output signal $y_2$ of the second target sound blocker 104(*n*) at the time n is expressed by noise(n), and the filter coefficient is expressed by $FN(n)=[hn_0(n), hn_1(n), \ldots, hn_{p-1}(n)]^T$, the signal e(n) after noise removal is calculated according to the following equations (5) to (7).

$$N(n)=[\text{noise}(n),\text{noise}(n-1), \ldots ,\text{noise}(n-p-1)]^T \tag{5}$$

$$e(n)=z(n)-FN^T(n)\cdot N(n) \tag{6}$$

$$FN(n+1)=FN(n)+\mu\cdot ne(n)\cdot N(n)/N^T(n)N(n) \tag{7}$$

Although the example of using LMS as the adaptive filter of each of the first target sound blocker 103 and the second target sound blocker 104 and using NLMS as the adaptive filter of the noise learner 106 is shown in the above-mentioned explanation, each of the adaptive filters can be alternatively constructed by using another adaptive filter, such as RLS (Recursive Least Squares) or an affine projection filter.

As mentioned above, because the beam-forming device in accordance with this Embodiment 1 is constructed in such a way as to apply the filter coefficient which the first target sound blocker 103 has learned as the filter coefficient of the phase synchronizer 105, a signal having a better SN ratio compared with those provided by a generalized sidelobe canceller (GSC) and a fixed beamformer can be acquired from the phase synchronizer 105. Further, because the coefficient acquired in the arithmetic process by the first target sound blocker 103 can be applied as the filter coefficient of the phase synchronizer 105, the phase synchronization process can be performed efficiently.

In addition, because the beam-forming device in accordance with this Embodiment 1 is constructed in such a way that the noise learner 106 learns the noise component included in the output signal of the phase synchronizer 105 and subtracts the learned noise component, the noise can be suppressed and a signal having an improved SN ratio can be acquired.

Embodiment 2

Figure 2:
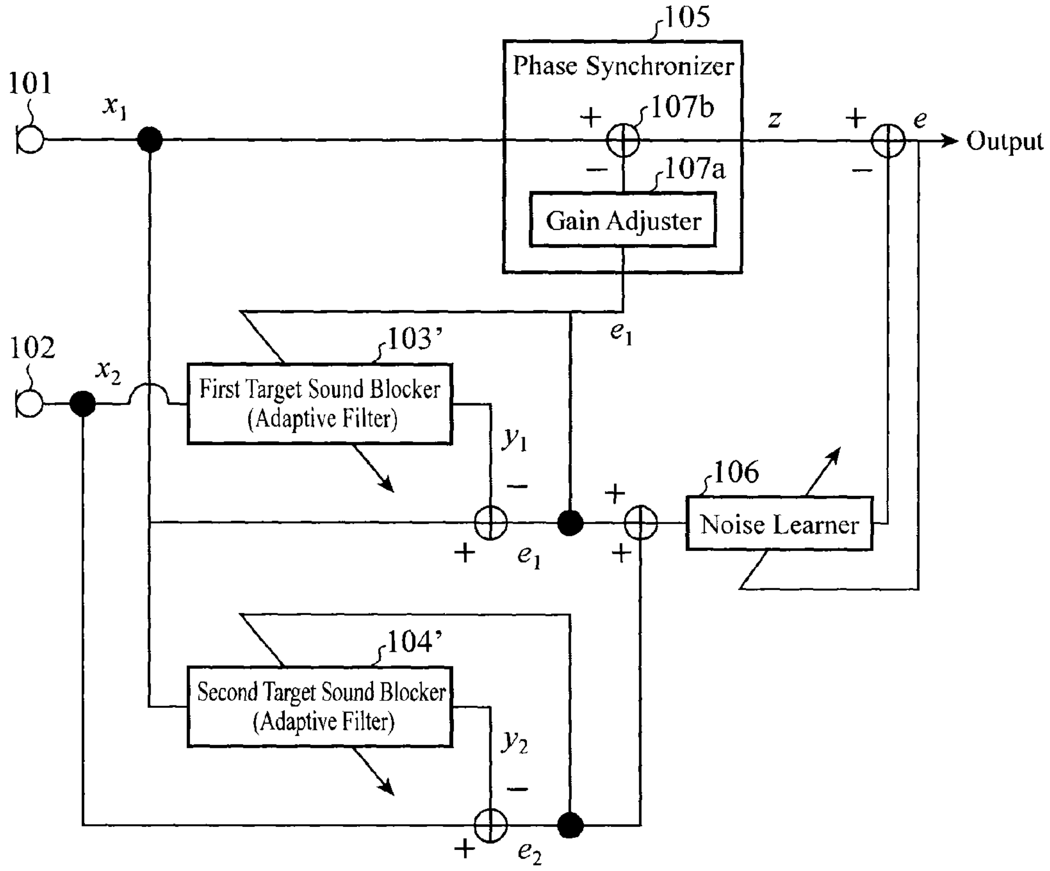
FIG. 2 is a view showing the structure of a beam-forming device in accordance with Embodiment 2.

FIG. 2 is a view showing the structure of a beam-forming device in accordance with Embodiment 2 of the present invention. In this Embodiment 2, a first target sound blocker 103' and a second target sound blocker 104' each of which uses an adaptive filter are disposed, and a phase synchronizer 105, which is shown in Embodiment 1, is comprised of a gain adjuster 107*a* and a synthesizer 107*b*.

Hereafter, the same components as those of the beamforming device in accordance with Embodiment 1 or like components are designated by the same reference numerals as those used in Embodiment 1, and the explanation of the components will be omitted or simplified.

The first target sound blocker 103' is comprised of an adaptive filter, and estimates a noise component $y_1$ included in a signal $x_1$ of a first microphone 101 from the signal $x_1$ of the first microphone 101 and a signal $x_2$ of a second microphone 102. By removing the estimated noise component $y_2$ from the signal $x_1$ of the first microphone 101, a signal $e_1$ after sound removal is acquired. The second target sound blocker 104' is comprised of an adaptive filter, and estimates a noise component $y_2$ included in the signal $x_2$ of the second microphone 102 from the signal $x_1$ of the first microphone 101 and the signal $x_2$ of the second microphone 102. By removing the estimated noise component $y_2$ from the signal $x_2$ of the second microphone 102, a signal $e_2$ after sound removal is acquired.

The gain adjuster 107*a* adjusts the gain of the output signal $y_1$ of the first target sound blocker 103', and the synthesizer 107*b* subtracts the signal whose gain is adjusted from the signal $x_1$ of the first microphone 101. As a result, a signal which is the same as the output signal z of the phase synchronizer 105 in accordance with Embodiment 1 is acquired. A noise learner 106 learns a noise component from the output signal z after gain adjustment by using a sum signal which is the sum of the signal $e_1$ after sound removal of the first target sound blocker 103' and the signal $e_2$ after sound removal of the second target sound blocker 104'. By subtracting an output signal of the noise learner 106 from the output signal z after gain adjustment, a signal e from which noise is removed can be acquired.

Although the example of performing a convolution operation by using the FIR filter in the phase synchronizer 105 is shown in above-mentioned Embodiment 1, the convolution operation using the FIR filter becomes unnecessary when an adaptive filter is used for each of the first target sound blocker 103' and the second target sound blocker 104', as shown in this Embodiment 2, an output signal z (n) can be acquired by using the output of the first target sound blocker 103' and the gain adjuster 107*a* according to the following equations (8) and (9) that are calculated on the basis of the above-mentioned equations (2) and (4).

First, the following equation (8) is acquired from the above-mentioned equation (2).

$$F^T(n)\cdot X_2(n)=x_1(n)-e_1(n) \tag{8}$$

Using the above-mentioned equations (4) and (8), the output signal z (n) is expressed by the signal $x_1$(n) of the first microphone 101 and the signal $e_1$(n) after sound removal on which the gain adjustment is performed, as shown in the following equations (9).

$$\begin{aligned} z(n) &= (x_1(n) + F^T(n)\cdot X_2(n))/2 \\ &= (x_1(n) + x_1(n) - e_1(n))/2 \\ &= x_1(n) - e_1(n)/2 \end{aligned} \tag{9}$$

As shown in the equation (9), after the signal $e_1$(n) after sound removal is outputted to the gain adjuster 107*a* and the gain adjuster 107*a* adjusts the gain of the signal $e_1$(n) to ½, the output signal z(n) is acquired by subtracting the signal from the signal $x_1$(n) of the first microphone 101. Although the case in which the gain in the gain adjuster 107*a* is set to ½ in the equation (9) in order to acquire the same result as that acquired in above-mentioned Embodiment 1 is shown, the numerical value can be changed properly according to the gain balance between the first microphone 101 and the second microphone 102, etc.

As mentioned above, because the beam-forming device in accordance with this Embodiment 2 is constructed in such a way that the noise component included in the signal of the first microphone 101 and the signal of the second microphone 102 is estimated by using adaptive filters as the first target sound blocker 103' and the second target sound blocker 104', and the gain adjuster 107*a* adjusts the gain of the signal after sound removal and subtracts this signal from the signal of the first microphone 101, it is not necessary to dispose an FIR filter for performing phase synchronization, and the amount of computations can be reduced.

Embodiment 3

Although the structure equipped with the following two microphones: the first microphone 101 and the second microphone 102 is shown in above-mentioned Embodiments 1 and 2, a beam-forming device in which the number of microphones is increased to N which is three or more will be explained in this Embodiment 3.

Figure 3:
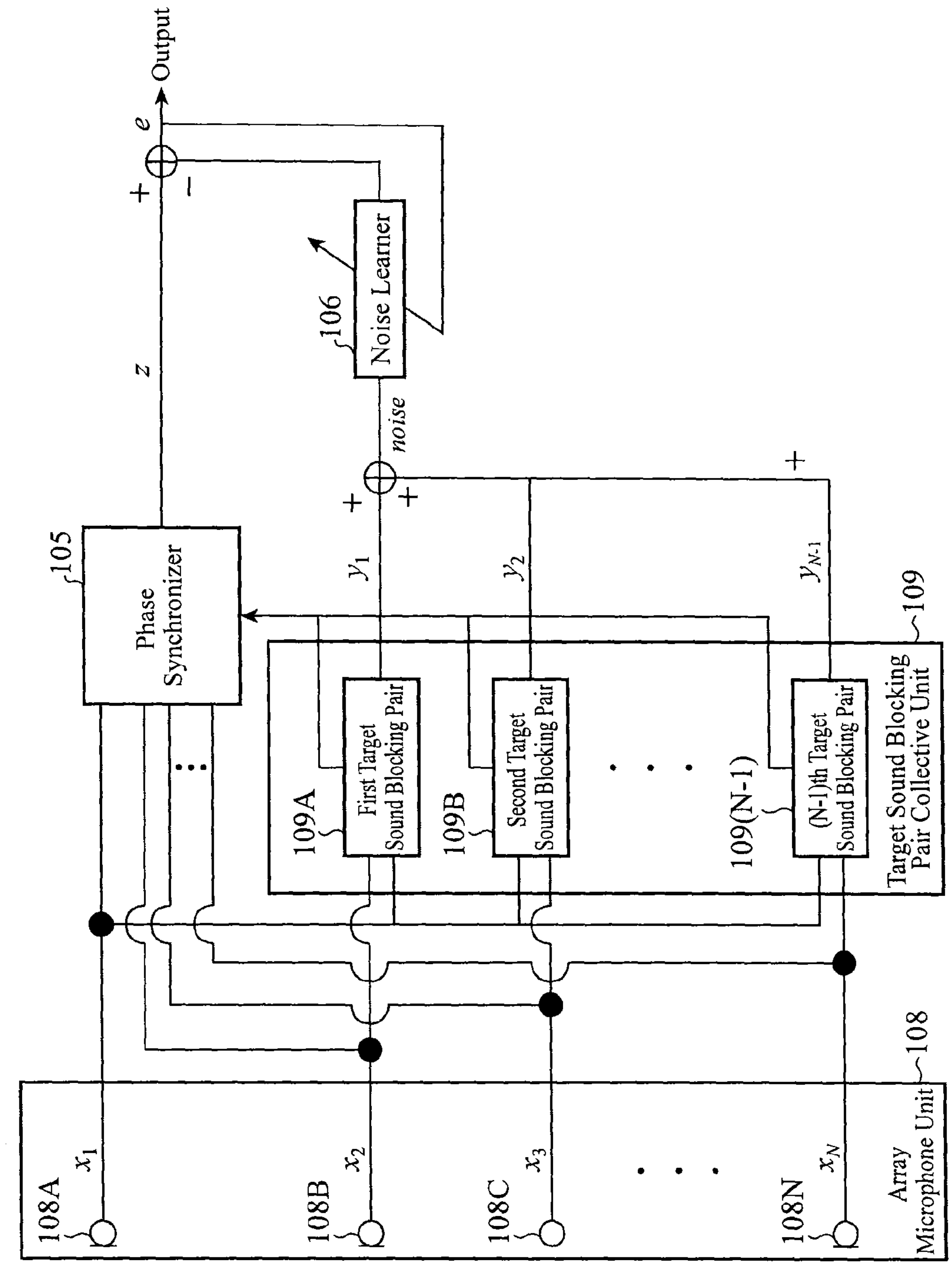
FIG. 3 is a view showing the structure of a beam-forming device in accordance with Embodiment 3.

FIG. 3 is a view showing the structure of the beam-forming device in accordance with Embodiment 3 of the present invention.

The beam-forming device in accordance with Embodiment 3 is comprised of an array microphone unit 108, a target sound blocking pair collective unit 109, a phase synchronizer 105, and a noise learner 106.

The array microphone unit 108 is comprised of the following N microphones: a first microphone 108A, a second microphone 108B, . . . , and an Nth microphone 108N. Each of the microphones 108A, 108B, . . . , and 108N converts an external sound into an electric signal. The target sound blocking pair collective unit 109 is provided with N−1 target sound blocking pairs with respect to the number N of microphones. In the example of FIG. 3, the unit consists of a first target sound blocking pair 109A, a second target sound blocking pair 109B, . . . , an (N−1)th target sound blocking pair 109(N−1). The target sound blocking pairs 109A, 109B, . . . , and 109 (N−1) remove a signal (target signal) having a correlation mutually by using both a signal (representative sound signal) of the first microphone 108A, and signals (a plurality of other sound signals) of the other microphones 108B, . . . , and 108N, respectively.

Figure 4:
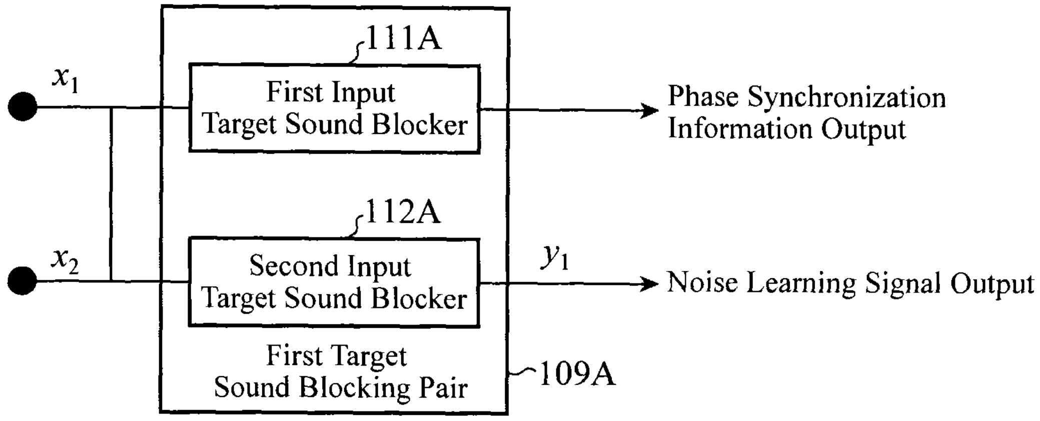
FIG. 4 is a view showing the structure of a target sound blocking pair of the beam-forming device in accordance with Embodiment 3.

FIG. 4 is a view showing the structure of each of the target sound blocking pairs of the beam-forming device in accordance with Embodiment 3 of the present invention. In FIG. 4, the first target sound blocking pair 109A is shown as an example.

The first target sound blocking pair 109A is comprised of a first input target sound blocker 111A and a second input target sound blocker 112A. The first input target sound blocker 111A blocks the target sound from the signal $x_1$ of the first microphone 108A, and outputs information for performing phase synchronization in the phase synchronizer 105. The second input target sound blocker 112A blocks the target sound from the signal $x_2$ of the second microphone 108B, and outputs a signal for learning noise in the noise learner 106.

The phase synchronizer 105 performs phase synchronization on signals inputted thereto from the N microphones 108A, 108B, . . . , and 108N by using results inputted thereto from the N−1 target sound blocking pairs 109A, 109B, . . . , and 109 (N−1). The noise learner 106 learns a noise component from an output signal of the phase synchronizer 105 by using a sum signal which is the sum of the signals outputted from the N−1 target sound blocking pairs 109A, 109B, . . . , and 109 (N−1).

The first input target sound blocker 111K in the Kth target sound blocking pair 109K (1≤K≤N−1) performs a learning process of removing the target signal from the signal $x_1$ of the first microphone 108A by using an adaptive filter according to NLMS, as shown in the following equations (10) to (12), like the above-mentioned equations (1) to (3), with the signal $x_1$ of the first microphone 108A being set as a teacher signal and the signal $x_{K+1}$ of the (K+1)th microphone being set as an input signal.

$$X_K(n)=[x_K(n),x_K(n-1), \ldots ,x_K(n-p-1)]^T \quad (10)$$

$$(n)=x_1(n)-y_{1K}(n)=x_1(n)-F_K^T(n)\cdot X_K(n) \quad (11)$$

$$F_K(n+1)=F_K(n)+\mu\cdot e_{1K}(n)\cdot X_K(n) \quad (12)$$

In the above-mentioned equations (10) to (12), $X_K$ is the signal $x_{K+1}$ of the (K+1)th microphone, $F_K$ is a filter coefficient of NLMS, and $y_{1K}$ is a residual signal in NLMS.

On the other hand, the second input target sound blocker 112K in the Kth target sound blocking pair 109K performs a learning process reverse to that shown by the above-mentioned equations (10) to (12) according to the following equations (13) to (15) with the signal $x_1$ of the first microphone 108A being set as an input signal and the signal $x_{K+1}$ of the (K+1)th microphone being set as a teacher signal.

$$X_1(n)=[x_1(n),x_1(n-1), \ldots ,x_1(n-p-1)]^T \quad (13)$$

$$e_K(n)=x_K(n)-y_K(n)=x_K(n)-F_{1K}^T(n)\cdot x_1(n) \quad (14)$$

$$F_{1K}(n+1)=F_{1K}(n)+\mu\cdot e_K(n)\cdot X_1(n) \quad (15)$$

In the above-mentioned equations (13) to (15), $X_1$ is the signal of the first microphone 101, $F_{1K}$ is the filter coefficient of NLMS, and $y_K$ is an output signal of the Kth target sound blocking pair 109K, i.e., a residual signal.

The phase synchronizer 105 adds a signal which the phase synchronizer acquires by carrying out convolution on an output signal of the first input target sound blocker 111A, i.e., output signals of microphones from the second microphone 108B to the Nth microphone by using an FIR filter having $F_K$ as a coefficient to the signal $x_1$ of the first microphone 108A.

The noise learner 106 receives, as its input, a noise signal noise which is the sum of the output signals $y_1, y_2, \ldots, y_{N-1}$ which are outputted from the second input target sound blockers 112A, 112B, . . . , and 112(N−1) of the first through (N−1)th target sound blocking pairs 109A, 109B, . . . , and 109 (N−1) and in which the target sound is blocked, and learns the noise component included in the output signal z of the phase synchronizer 105 by using an NLMS adaptive filter that assumes the output signal z of the phase synchronizer 105 as the target signal. By subtracting the output signal of the noise learner 106 from the signal of the phase synchronizer 105, a signal e from which the noise is removed can be acquired.

As mentioned above, because the beam-forming device in accordance with Embodiment 3 is constructed in such a way that the beam-forming device includes the array microphone unit 108 comprised of the N microphones whose number is three or more, and the target sound blocking pair collective unit 109 comprised of the N−1 target sound blocking pairs, and each of the target sound blocking pairs includes the first input target sound blocker that receives a signal of a representative microphone and signals of the other microphones as its input, and removes a target signal from the signal of the representative microphone, and the second input target sound blocker that removes the target signal from the input signal of each of the other microphones, the device equipped with the three or more microphones, too, can improve the accuracy of phase synchronization. Further, efficient phase synchronization can be carried out.

Although the example of constructing the target sound blocking pair collective unit 109 by using both the signal of the first microphone 108A which is the representative microphone and the signals of the other microphones 108B, . . . , and 108N is shown in above-mentioned Embodiment 3, the representative microphone can alternatively consist of a microphone other than the first microphone 108A. For example, switching among the microphones, such as a selection of a microphone having the highest SN ratio as the representative microphone, can be carried out according to surrounding conditions.

Further, although the example of using LMS as each adaptive filter is shown in above-mentioned Embodiment 3, each adaptive filter can be alternatively constructed by using another algorithm, such as NLMS or an affine projection filter.

Embodiment 4

Figure 5:
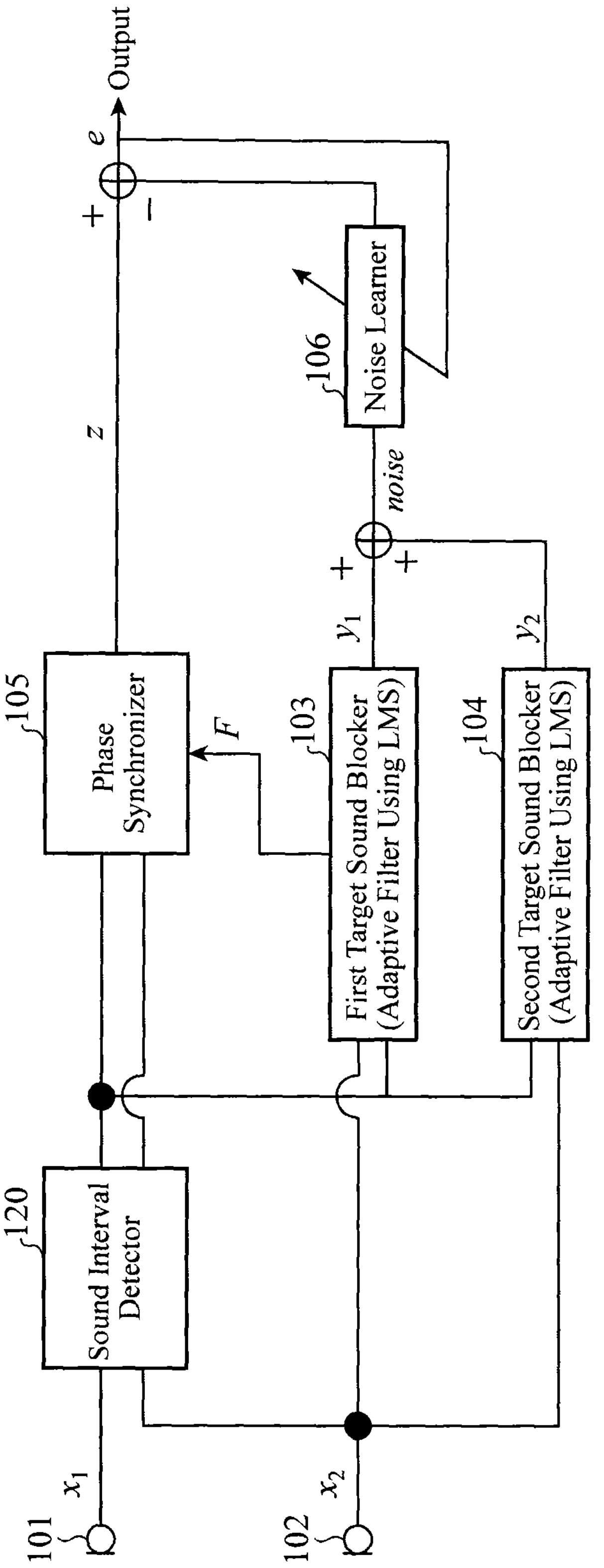
FIG. 5 is a view showing the structure of a beam-forming device in accordance with Embodiment 4.
Figure 6:
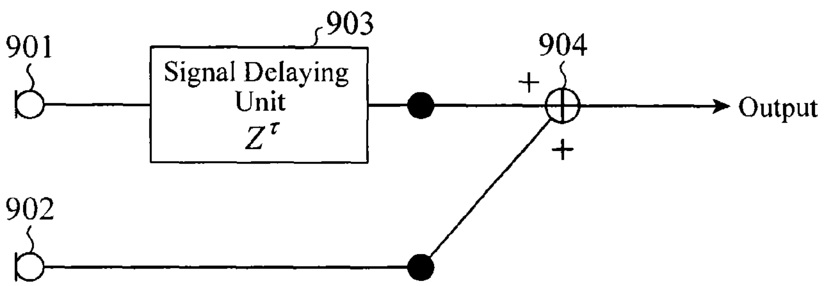
FIG. 6 is a view showing the structure of a fixed beam-former using Delay and Sum.
Figure 7:
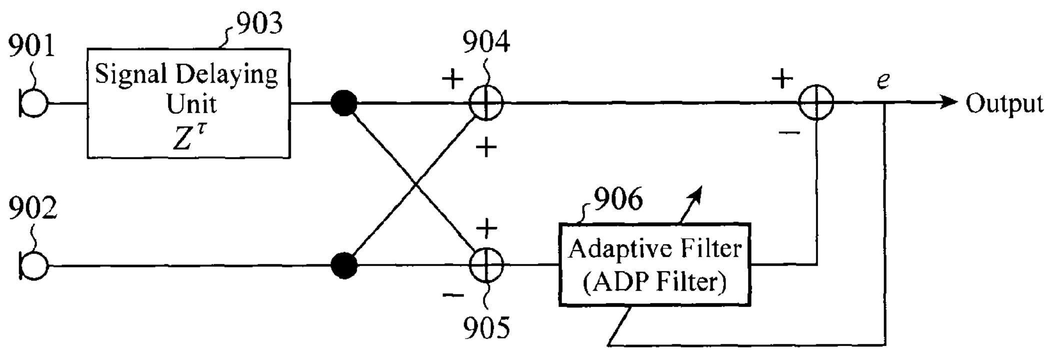
FIG. 7 is a view showing the structure of a generalized sidelobe canceller.

FIG. 5 is a view showing the structure of a beam-forming device in accordance with Embodiment 4 of the present invention. In this Embodiment 4, a sound interval detector 120 is disposed additionally in the beam-forming device shown in above-mentioned Embodiment 1.

The sound interval detector 120 receives a signal of a first microphone 101 and a signal of a second microphone 102 as its input, and detects a sound interval of each of the inputted signals. A known technique can be applied to the detection of a sound interval. For example, a detection technique which a sound interval discriminating device, disclosed by reference 1 shown below, uses can be applied.

Reference 1: Japanese Unexamined Patent Application Publication No. Hei 10-171487

A first target sound blocker 103 and a second target sound blocker 104 can be constructed in such a way as to refer to the detection results of the sound interval detector 120, and, when the detection results showing that it is a sound interval are inputted, perform a learning process of learning an adaptive filter; otherwise, not perform the learning process of learning the adaptive filter.

As mentioned above, because the beam-forming device in accordance with Embodiment 4 is constructed in such a way that the beam-forming device includes the sound interval detector 120 that detects a sound interval of each of the signals of the first and second microphones 101 and 102, and the first and second target sound blockers 103 and 104 refer to the detection results of the sound interval detector 120, and, only when the detection results showing that it is a sound interval are inputted, perform the learning process of learning the adaptive filter, erroneous learning of the adaptive filter can be prevented and the filter coefficient can be learned with a higher degree of accuracy.

Although the example of applying the sound interval detector 120 to the beam-forming device shown in Embodiment 1 is shown in above-mentioned Embodiment 4, the sound interval detector can also be applied to the beam-forming device shown in Embodiments 2 and 3.

While the invention has been described in its preferred embodiments, it is to be understood that an arbitrary combination of two or more of the above-mentioned embodiments can be made, various changes can be made in an arbitrary component in accordance with any one of the above-mentioned embodiments, and an arbitrary component in accordance with any one of the above-mentioned embodiments can be omitted within the scope of the invention.

INDUSTRIAL APPLICABILITY

Because the beam-forming device in accordance with the present invention can carry out phase synchronization in a fixed beamformer with a high degree of accuracy, the beam-forming device is suitable for use in a sound system having a function of carrying out high-accuracy beamforming which is not affected by variations in a sound field environment.

EXPLANATIONS OF REFERENCE NUMERALS

101 first microphone, 102 second microphone, 103, 103' first target sound blocker, 104, 104' second target sound blocker, 105 phase synchronizer, 106 noise learner, 107*a* gain adjuster, 107*b* synthesizer, 108 array microphone unit, 109 target sound blocking pair collective unit, 109A first target sound blocking pair, 111A first input target sound blocker, 112A second input target sound blocker, 120 sound interval detector.

The invention claimed is:

1. A beam-forming device that performs an arithmetic process on an inputted sound signal to form a directional characteristic, said beam-forming device comprising:

- a first target sound blocker and a second target sound blocker that remove a target signal having a correlation mutually from a first sound signal and a second sound signal into which sounds collected by different microphones are converted respectively;
- a phase synchronizer that synchronizes phases of said first sound signal and said second sound signal and synthesizes these sound signals by using information acquired when said first target sound blocker removes said target signal; and
- a noise learner that learns a noise component included in an output signal of said phase synchronizer from signals from which said target signal is removed by said first target sound blocker and said second target sound blocker.

2. The beam-forming device according to claim 1, wherein said first target sound blocker and said second target sound blocker learn filter coefficients when removing said target signal from said first sound signal and said second sound signal, and said phase synchronizer convolves the filter coefficient which said first target sound blocker has learned with said second sound signal and adds the second sound signal with which said filter coefficient is convolved to said first sound signal to synchronize the phases.

3. The beam-forming device according to claim 1, wherein said first target sound blocker and said second target sound blocker are comprised of adaptive filters that estimate noise components included in said second sound signal and said first sound signal, and said phase synchronizer includes an adjuster that adjusts a gain of a sound removed signal which is calculated on a basis of the noise component estimated by said first target sound blocker, and subtracts the sound removed signal whose gain is adjusted by said adjuster from said first sound signal.

4. A beam-forming device that performs an arithmetic process on an inputted sound signal to form a directional characteristic, said beam-forming device comprising:

a target sound blocking pair collective unit that is comprised of N−1 target sound blocking pairs that remove a target signal having a correlation mutually from a representative sound signal and a plurality of other sound signals into which sounds collected by N (N≥3) microphones are converted respectively;

a phase synchronizer that synchronizes phases of said representative sound signal and said plurality of other sound signals and synthesizes said sound signals by using information acquired when said N−1 target sound blocking pairs remove said target signal; and a noise learner that learns a noise component included in an output signal of said phase synchronizer from signals from which said target signal is removed by said N−1 target sound blocking pairs, wherein each of said N−1 target sound blocking pairs includes a first input target sound blocker that removes said target signal from said representative sound signal, and a second input target sound blocker that removes said target signal from either one of said plurality of other sound signals.

5. The beam-forming device according to claim 4, wherein said phase synchronizer convolves a filter coefficient which each of the first input target sound blockers of said N−1 target sound blocking pairs has learned when removing said target signal from said representative sound signal with said plurality of other sound signals, and adds the sound signals with which said filter coefficient is convolved to said representative sound signal to synchronize the phases.

6. The beam-forming device according to claim 2, wherein said beam-forming device includes a sound interval detector that detects a sound interval included in said first sound signal and said second sound signal, and said first target sound blocker and said second target sound blocker learn said filter coefficients when a sound interval is detected by said sound interval detector.

7. The beam-forming device according to claim 3, wherein said beam-forming device includes a sound interval detector that detects a sound interval included in said first sound signal and said second sound signal, and said first target sound blocker and said second target sound blocker estimate the noise component by using said adaptive filters when a sound interval is detected by said sound interval detector.

8. The beam-forming device according to claim 5, wherein said beam-forming device includes a sound interval detector that detects a sound interval included in said representative sound signal and said plurality of other sound signals, and said N−1 target sound blocking pairs learn said filter coefficient when a sound interval is detected by said sound interval detector.

* * * * *